| United States Patent [19] | [11] | 4,339,453 |
|---|---|---|
| Grier et al. | [45] | Jul. 13, 1982 |

[54] ANTIMICROBIAL AMINOPYRIMIDINIUM SALTS

[75] Inventors: Nathaniel Grier, Englewood; Elbert E. Harris, Westfield; Henry Joshua, Elizabeth; Arthur A. Patchett, Westfield; Bruce E. Witzel, Rahway; Richard A. Dybas, Somerville, all of N.J.

[73] Assignee: Merck & Co., Inc., Rahway, N.J.

[21] Appl. No.: 59,812

[22] Filed: Jul. 23, 1979

[51] Int. Cl.³ .................. A01N 21/02; C07D 239/42
[52] U.S. Cl. .................................. 424/251; 71/92; 71/88; 71/95; 544/296; 544/320; 544/321; 544/323; 544/325; 544/326; 544/329; 162/161; 210/764
[58] Field of Search .............. 544/296, 320, 321, 325, 544/323, 326, 329; 71/92; 424/251

[56] References Cited

U.S. PATENT DOCUMENTS

| 2,674,598 | 4/1954 | Kyrides et al. | 544/323 |
|---|---|---|---|
| 2,983,727 | 5/1961 | Lyttle et al. | 544/323 |
| 3,452,143 | 6/1969 | Grier | 424/325 |
| 3,626,060 | 12/1971 | Grier | 424/232 |
| 3,670,077 | 6/1972 | Freeman et al. | 544/323 |
| 4,116,674 | 9/1978 | Sunley et al. | 544/326 |

OTHER PUBLICATIONS

Grier et al., "Journal of Coating Technology", vol. 52, No. 671, 1980, pp. 57–63.
Brown, *The Pyrimidines*, Sup. I, 1970, Wiley-Interscience, N.Y., pp. 10, 276–281.

*Primary Examiner*—Glennon H. Hollrah
*Assistant Examiner*—James H. Turnipseed
*Attorney, Agent, or Firm*—Raymond M. Speer; Edmunde D. Riedl

[57] ABSTRACT

4-Amino- and 2,4-diaminopyrimidines with a quaternized ring nitrogen and an oxygen bearing substituent such as hydroxyalkyl, alkoxyalkyl, or alkanoyl on one of the exo- or endocyclic nitrogens and a $C_{6-18}$ alkyl on another, are highly active antimicrobial agents with a relatively low acute mammalian toxicity.

20 Claims, No Drawings

ANTIMICROBIAL AMINOPYRIMIDINIUM SALTS

BACKGROUND OF THE INVENTION

This invention is concerned with 4-amino and 2,4-diaminopyrimidines of general structural formula:

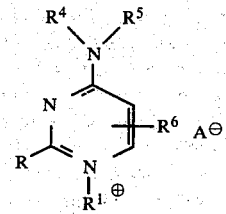

wherein R is hydrogen, lower alkyl or

one of $R^1$-$R^5$ is $C_{6-18}$ alkyl and one other is an oxygen bearing substituent such as hydroxyalkyl, alkoxyalkyl or alkanoyl, which are useful as antimicrobial agents especially as fungicides.

There are numerous compounds known in the art with similar structures and many of them are known to be antimicrobial agents, such as those disclosed in U.S. Pat. No. 2,674,598, German Offen. No. 2,403,165, Chem. Abstr. 82, 107423k (1975), South African Pat. No. 7,500,491, and Belgian Pat. No. 831,938.

However, none of the prior art compounds have all three of the limitations that are imposed on the novel compounds of this invention:

(1) one of the nitrogen substituents is a $C_{6-18}$ alkyl;
(2) one of the nitrogen substituents is oxygen bearing; and
(3) at least one exocyclic nitrogen is secondary or tertiary. And surprisingly, it has been found that 4-amino- and 2,4-diamino compounds with these limitations have much greater antimicrobial activity and much less mammalian toxicity than compounds without said structural limitations.

Accordingly it is an object of this invention to provide novel compounds of the above general description, processes for preparing the novel compounds, formulations of the novel compounds for use as antimicrobial agents, and a novel method of inhibiting the growth of microbial organisms.

DETAILED DESCRIPTION OF THE INVENTION

This invention is concerned with novel compounds of structural formula:

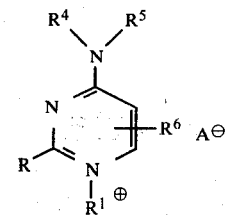

wherein:
R is hydrogen, $C_{1-5}$ alkyl, or $R^2R^3N-$;
$R^1$ is
 (1) $C_{1-18}$ alkyl, either straight or branched-chain, either unsubstituted or substituted with
   (a) hydroxy-,
   (b) $C_{1-3}$ alkoxy-,
   (c) carboxy-,
   (d) $C_{1-3}$ alkoxycarbonyl-,
   (e) phenyl-$C_{1-3}$ alkoxycarbonyl-,
   (f) $C_{2-5}$ alkanoyloxy-,
   (g) $C_{3-6}$ cycloalkyl-,
   (h) gem-di($C_{1-3}$ alkoxy)-,
   (i) a heterocycle of 5–6 members such as tetrahydrofuran, pyrimidin-2,4-dion-6-yl, and pyroglutamyl,
   (j) phenyl, either unsubstituted or substituted with
      (i) $C_1$-$C_{12}$ alkoxy, or
      (ii) $C_{1-5}$ alkyl,
   (k) amino,
   (l) hydroxy-$C_{1-3}$ alkoxy, or
   (m) $C_{2-3}$ alkanoyl;
 (2) $C_{3-5}$ alkenyl, or
 (3) $C_{1-3}$ alkoxycarbonyl-$C_{2-5}$ alkenyl;
$R^2$, $R^3$, $R^4$ and $R^5$ are independently hydrogen, or $R^1$;
$R^6$ is
 (1) hydrogen;
 (2) $C_{1-11}$ alkyl, especially $C_{1-5}$ alkyl, either straight or branched-chain, and either unsubstituted or substituted with $C_{1-5}$ alkoxy, or $C_{1-5}$ alkoxycarbonyl;
 (3) $C_{1-3}$ alkylsulfinyl;
 (4) halo, such as chloro, bromo, or iodo; or
 (5) $-(CH_2)_3-$ or $-(CH_2)_4-$ joined to the 5 and 6 carbons of the pyrimidine ring; and $A^\ominus$ is non-toxic anion derived from an organic or inorganic acid, especially halide such as $Cl^\ominus$, $Br^\ominus$, $I^\ominus$, $C_{2-5}$ alkanoyloxy, or nitrate, with the proviso that, (1) at least one of $R^1$, $R^2$, $R^3$, $R^4$ or $R^5$ is $C_{6-18}$ alkyl;
(2) at least one of $R^1$, $R^2$, $R^3$, $R^4$ or $R^5$ is oxygen-bearing, and
(3) at least one exocyclic nitrogen is a secondary or tertiary amine.

In a preferred embodiment of the novel compounds of this invention, R represents $R^2R^3N-$.

In a still more preferred embodiment, R represents $R^2R^3N-$; $R^1$ is $C_{1-5}$ alkyl, either unsubstituted or substituted with hydroxy, or $C_{3-5}$ alkenyl; one of $R^2R^3N-$ and $R^4R^5N$ is hydroxy-$C_{1-5}$ alkyl-NH— and the other is $C_{12}$ alkyl-NH— or di($C_6$ alkyl)N-; $R^6$ is hydrogen, or $C_{1-3}$ alkyl; and $A^\ominus$ is halide, or acetate.

The novel compounds of this invention are depicted as aminopyrimidinium salts. However, it is well known that other tautomeric forms such as the iminodihydropyrimidinium structure, among others, may better represent the predominant species. For example:

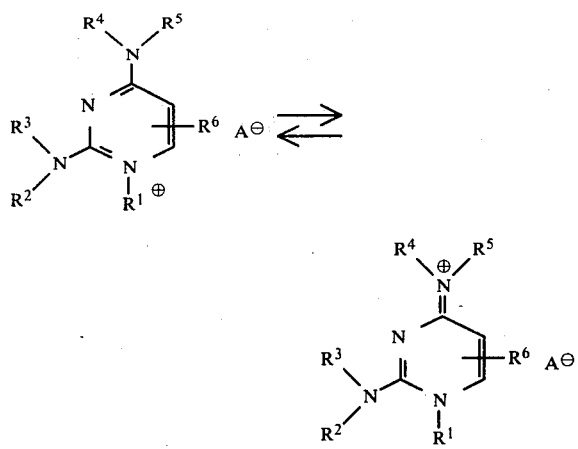

Generally, the compounds of this invention may be prepared using from two to four or more chemical steps. One scheme utilizes the reaction of 2,4-dichloropyrimidine with the appropriate amines in at least a 1:1 molar ratio respectively, (A.)
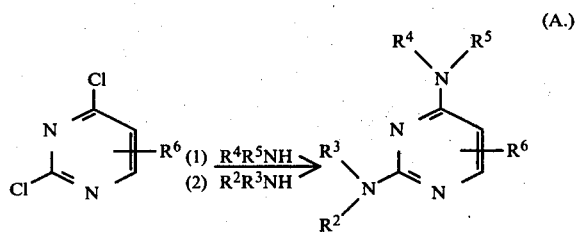

The last step, with the free base and an alkylating agent, comprises (B.)
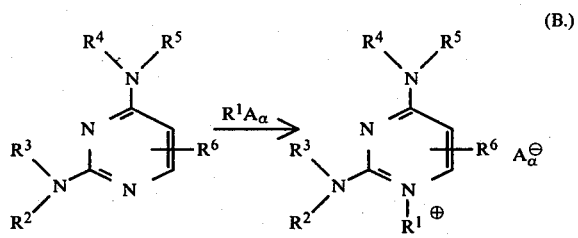

wherein $A_\alpha$ is Cl, Br, I, sulfate, $C_{1-3}$ alkanesulfonate, benzenesulfonate or toluenesulfonate.

Although $R^1$ is represented as a substituent on ring nitrogen one, it may in some cases actually be on ring nitrogen three. However, the useful properties obtained with these derivatives do not appear to be altered significantly, and the less hindered ring nitrogen would appear to be favored for the reaction. It is possible moreover for an exo nitrogen to react preferentially with the alkylating agent. $A_\alpha\ominus$ may be converted to the desired $A\ominus$ by procedures described below.

A variety of solvents may be used as a reaction medium for the 2,4-dichloropyrimidines and amines of Step A. These include $C_{1-4}$ alcohols such as methyl, ethyl, isopropyl, n-propyl and butyl; aromatic hydrocarbons such as benzene, toluene, chlorobenzene or the like; ketones, such as acetone, methyl ethyl ketone, or mixtures of these, amides such as dimethylformamide or N-methylpyrrolidone. The replacement of the 4-chloro group usually takes place more readily than the 2-chloro group, and this property is taken advantage of to prepare those compounds wherein $R^2R^3N—$ is dissimilar to $R^4R^5N—$. Reaction temperatures range from 10°–100° C. or higher and reaction times are in the range of 4–20 hours. Excess amine may be used as a scavenger for liberated hydrogen chloride. The progress of the reaction may be monitored by thin layer chromatography on silica gel plates using among other solvent systems, chloroform:methanol-ammonia (15:4:1 by volume). Usually, the end products have lower $R_f$ than the starting materials. The products are generally solids which precipitate, especially if solutions are concentrated and cooled, and can be isolated by filtration. Additional crops can be isolated from filtrates by further concentration and mixing with acetone followed by chilling. Some of the syntheses may be accomplished in the absence of solvents with an excess of amine serving also as the reaction medium.

Still other methods for preparing the compounds of this invention are known in the art and include primary syntheses, that is, formation of the substituted pyrimidine ring from acyclic intermediates; or by replacement of alkoxy, mercapto, alkylthio, alkylsulphonyl or alkylsulphinyl pyrimidines with amines, or by transamination. The last procedure utilizes aminopyrimidine salts such as the hydrochloride and excess of amine with heating at 140°–200° C. for 2–30 hours in a closed system with more volatile amines. Interestingly, 4-methylsulfonyl- and 4-methylsulfinylpyrimidine undergo aminolysis more rapidly than the 2-substituted derivatives.

The final alkylating process (B) is run in the same solvent systems as the initial dichloropyrimidine-amine reaction, or an excess of the alkylating agent is used as the medium. Generally, the salt-like products are soluble in hot lower alkanols and crystallize on cooling. Acetone, diethyl ether, dioxane and the like may be used to decrease solubility whereas water enhances it. Reaction times may vary from 1 to 24 or more hours and temperatures may range from 20° C. to 150° C. or thereabout. Recrystallization in the presence of decolorizing carbon serves as a useful purification and solvents of utility include the $C_{1-4}$ alkanols, with or without admixture with ethyl acetate, acetone or diethyl ether and occasionally water.

The anion may be replaced by other salt-forming groups using conventional methods well known in the art. Halide salts in aqueous medium may be treated with appropriate silver salts to provide insoluble silver halide and the corresponding pyrimidinium salt, for example, with silver nitrate the nitrate salt. Ion exchange resins provide another route, preloading of a column containing the resin with a solution of the desired anion which may be inorganic or organic and passage of the pyrimidinium salt over the treated resin permits quantitative exchange. Still other procedures are useful. Water-soluble pyrimidinium salts reacted with alkali salts of desired anions, for example saccharinate, lauryl sulfate, lauryl ether sulfate, salicylate, pamoate are converted to the water-insoluble salt derivatives which are isolated simply by filtration followed by a water wash. These and other methods are readily employed to secure the desired salts of this invention.

Suitable anions, $A\ominus$, for salt formation include those derived from inorganic as well as those from organic acids such as for example halide e.g. chloride, bromide, and iodide, sulfate, bisulfate, phosphate, nitrate, acetate, propionate, butyrate, palmitate, stearate, ascorbate, glycollate, lactate, citrate, tartrate, gluconate, maleate, fumarate, succinate, carbonate, bicarbonate, benzoate, phthalate, nicotinate and the like. Generally, any anion derived from an acid is suitable and satisfactory, low toxicity types being preferred. The anion selection is based in part upon desired solubilities in aqueous or solvent media, to improve compatibilities with other ingredients of the formulation, for enhanced compound stability, to lower toxicity still further, for prolonged action and to increase antimicrobial efficiency.

The novel compounds of this invention are useful as antimicrobial agents and have a low mammalian toxicity. Illustrative of the unusual performance/safety aspect is 4(dodecylamino)-2-(2-hydroxyethylamino)-1-methylpyrimidine hydroiodide, that is a 2,4-diaminopyrimidine in which $R^1$ is methyl, $R^2$ is 2-hydroxyethyl, $R^3$ is hydrogen, $R^4$ is n-dodecyl, $R^5$ is hydrogen, $R^6$ is hydrogen and $A^\ominus$ is iodide. Wheat plants were protected against a fungal rust, *Puccinia recondita* var. *tritici*, by first spraying with a solution containing 10 ppm of the novel cited pyrimidine and then after drying, the treated plant was dusted with spores of the fungus taken directly from diseased plants. After appropriate incubation at 70° F. and 95% relative humidity the plants were set in greenhouses for disease growth. There was an 80% decrease in leaf pustules for the treated plants as compared to untreated spore-sprayed control plants. In the same test, the well-known fungicide, maneb, provided only a 29% decrease in leaf pustules when used as a protectant at the same concentration. Moreover, the novel cited pyrimidine was non-phytotoxic at ten-fold and higher concentrations. In mice its acute toxicity, $LD_{50}$, given orally is greater than 500 mg/kg of body weight and subcutaneously, greater than 250 mg/kg when administered in water with 1% Tween 80 surfactant. In laboratory tests loadings of this novel pyrimidine compound at five pounds per 100 gallons of aqueous paints such as exterior polyvinyl acetate and acrylics provided protection against attack of the desired paint films from *Aureobasidium pullulans*, the fungus most commonly associated with disfigurement and degradation of exteriorly exposed painted surfaces. Other microorganisms which are inhibited by concentrations of 1–50γ/ml include *Staphylococcus aureus, Klebsiella aerogenes*, Bordetella sp., *Pasteurella multocida, E. coli*, Salmonella sp., *Pseudomonas aeruginosa*, Fusarium sp., Penicillium sp., *Candida albicans*, and fungi associated with biodeterioration or disease potential, when tested by conventional assays in medicated agar medium or dilution in broth. The novel compounds of this invention are useful as disinfectants, to inhibit slime formation in aqueous systems such as cooling tower waters, papermill process waters, such as white waters, in aqueous adhesives, coatings, pigment dispersions and in the protection of wood, leather, plastics, cotton and synthetic fibrous materials as well as living plants.

In one assay series using inhibitors of growth of *Aureobasidium pullulans* on paint films as the test system, no loss in high efficiency was observed for the following molecular modifications:

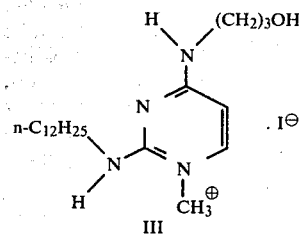

as compared to the novel, previously cited pyrimidine derivative. In the middle structure IV, a 6-methyl group has been introduced and although a steric factor is evident, the compound still performs well. Compound V, which has a methallyl on ring nitrogen 1, in place of a methyl group, still presents an acute oral $LD_{50}$ in mice of greater than 500 mg/kg of body weight. The same relatively low toxicity is maintained in a further variation illustrated by VI, another potent antimicrobial agent:

The active compounds can be prepared for agricultural use in the form of dusts, powders, pastes and various liquid concentrates which may be solutions or suspensions. The preparations preferably contain one or more of the usual emulsifiers, surfactants, suspending agents, melting agents, spreading agents, conditioning agents, sticking agents and the like to promote stability and uniform distribution in water or in the common organic solvents employed for spraying, and also spreading and adhesion. Both the powdered and liquid forms may be used for seed treatment, soil dosage, or foliar applications. The accessary agents required to formulate the active compounds may be selected from those described in U.S. Pat. No. 3,452,143 and U.S. Pat. No. 3,626,060. Surfactants can be anionic, non-ionic, or cationic, and the latter two types are preferred. Inert carriers are preferably kaolin clays to minimize adsorption, but silicas, talcs, diatomaceous earth, vermiculite and ground cobs are also useful. Sticking agents include glycerine, ethylene glycol and other polyglycols; adhesives may be resins, cellulose ether derivatives, waxes, and polyvinylpyrrolidone among others. Further, other agents may be included in the formulations such as additional antimicrobial agents, insecticides, nematocides, dyes and growth promotants.

The rates of use depend upon a number of factors but generally concentrations of the compound of this invention in the range of 5 to 250 ppm are effective against phytopathogenic bacteria and fungi. Usually, for seed treatments to protect against root rotting fungi such as *Rhizoctonia solani* about 5 to 50 ppm is sufficient and application may be made directly to seed. A dust formulation can be mixed with the seed in the common seed treater boxes, or a liquid concentrate can be sprayed on with a commercial-type machine. Usually about 0.5 to 2 fl. oz./bushel of seed is employed thereby avoiding a subsequent drying operation. Further, a wettable powder formulation may be suspended in water and sprayed directly in the furrows at planting time to provide seed and seedling protection. A 50% by weight of active antifungal pyrimidinium salt wettable powder composition mixed at the rate of 10 lbs. in 100 gallons of water and applied to a three inch depth in soil generally suffices for one acre as for various bean varieties (*Erysiphe polygoni*) or cucumbers.

Foliar treatments are comprised of wettable powders made into aqueous suspensions at the farm or solution concentrates dilutable with water prior to use which provide from 50 to 200 ppm on the plants and are useful in preventing powdery mildew of beans, bacterial leaf spot of peppers and tomatoes or a variety of fungal rusts on grain and other damaging infestations of plants and crops.

EXAMPLE 1

4-n-Dodecylamino-2-(2-hydroxyethylamino)-1-methylpyrimidinium Iodide

Step A: Preparation of 2-chloro-4-(n-dodecylamino)pyrimidine

To a well-stirred slurry of 2,4-dichloropyrimidine (27.0 g, 0.18 m) and n-butanol (150 ml) is added 150 ml of water followed immediately by n-dodecylamine (67.2 g, 0.36 m). The clear solution obtained after a short time gradually clouds as the product precipitates. After allowing to stir about 40 hours, the mixture is filtered, the semi-dry cake is flushed several times with small portions of water, washed twice with water and finally sucked dry to yield 29.2 g (64%) of 2-chloro-4-(n-dodecylamino)pyrimidine, m.p. 80°–82° C.

Alternately, one equivalent of another base (potassium carbonate, triethyl amine, etc.) as hydrogen chloride scavenger may be used in place of a second equivalent of n-dodecylamine.

Step B: Preparation of 4-(n-dodecylamino)-2-(2-hydroxyethylamino)pyrimidine

A mixture of 2-chloro-4-(n-dodecylamino)pyrimidine (6.0 g, 0.02 m), ethanolamine (12.2 g, 0.2 m), ethanol (70 ml) and water (20 ml) is stirred and refluxed until thin-layer chromatography (silica gel; 10 parts chloroform, 0.2 parts methanol, 0.5 parts concentrated ammonium hydroxide) indicates the absence of the 2-chloropyrimidine compound. The ethanol is removed in vacuo, the residue is distributed between water and methylene chloride, the aqueous layer is extracted again with methylene chloride, the combined organic layer is washed well with water, dried (Na$_2$SO$_4$) and concentrated to leave a residue of 6.3 g (98%) of 4-(n-dodecylamino)-2-(2-hydroxyethylamino)pyrimidine as an oil which crystallizes readily on standing.

Alternately, the residual mixture obtained after removal of the ethanol may be diluted with water, and the oily suspension thus obtained seeded with pure product to yield filterable material.

Step C: Preparation of 4-(n-dodecylamino)-2-(2-hydroxyethylamino)-1-methylpyrimidinium iodide Methyl iodide (0.8 ml, 0.012 m) is added to a stirred solution of 4-(n-dodecylamino)-2-(2-hydroxyethylamino)pyrimidine (3.2 g, 0.01 m) in anhydrous dimethylformamide (25 ml), and the stoppered solution allowed to stir overnight. Anhydrous ether (180 ml) is added slowly in small portions, and the resulting precipitate is allowed to age (stirring) for about one hour. The mixture is filtered, the mother liquors are displaced with small portions of ether, and the cake is washed well with ether and dried to yield 3.4 g (76%) of colorless 4-(n-dodecylamino)-2-(2-hydroxyethylamino)-1-methylpyrimidinium iodide, m.p. 118°–119° C.

EXAMPLE 2

2-n-Dodecylamino-1-(3-hydroxypropyl)-4-(3-hydroxypropylamino)pyrimidinium bromide

Step A: Preparation of 2-chloro-4-(3-hydroxypropylamino)pyrimidine 2,4-Dichloropyrimidine (4.5 g, 0.03 m) in an n-butanol (50 ml)-water (50 ml) mixture is reacted with 3-amino-1-propanol (4.5 g, 0.06 m) following the procedure of Example 1. After stirring at room temperature for 24 hours, water (200 ml) is added, the mixture is extracted with methylene chloride (3×200 ml), the combined organic extracts are washed well with water, dried, and concentrated. Recrystallization of the solid residue from methylene chloride/hexane yields 2.8 g of 2-chloro-4-(3-hydroxypropylamino)pyrimidine, m.p. 113°–114° C.

Step B: Preparation of 2-n-dodecylamino-4-(3-hydroxypropylamino)pyrimidine

A mixture of 2-chloro-4-(3-hydroxypropylamino)pyrimidine (37 g, 0.2 m), n-dodecylamine (81.5 g, 0.44 m), ethanol (2.5 l) and water (250 ml) is heated under reflux until thin layer chromatography (silica gel; 7.5 parts by volume chloroform, 0.5 parts by volume concentrated ammonium hydroxide, and 2.0 parts by volume methanol) indicates absence of the pyrimidine starting material. After concentration of the mixture, the residue is taken up in methylene chloride, and filtered from some n-dodecylamine hydrochloride. The organic solution is washed with water, dried and concentrated, and the residue is chromatographed on silica gel using a chloroform-ethanol eluant system (0–10% by volume of ethanol) to yield 56 g of 2-n-dodecylamino-4-(3-hydroxypropylamino)pyrimidine, m.p. 58°–59° C.

Step C: Preparation of 2-(n-dodecylamino)-1-(3-hydroxypropyl)-4-(3-hydroxypropylamino)pyrimidinium bromide A solution of 2-(n-dodecylamino)-4-(3-hydroxypropylamino)pyrimidine (0.67 g, 0.002 m) in dried dimethylformamide (10 ml) is treated with 3-bromo-1-propanol (0.31 g, 0.0022 m) and the resultant mixture is stirred at 35° C. until thin-layer chromatography (silica gel; 7.5 parts by volume chloroform, 0.5 parts by volume concentrated ammonium hydroxide, and 2.0 parts by volume methanol indicates the absence of starting pyrimidine. After cooling to room temperature, ether (50 ml) is added slowly to the mixture, the mixture is allowed to stir for 0.5 hour, the supernatant is decanted from the oil that separates, the oil is stirred vigorously with three separate portions of fresh ether, and then pumped dry to yield 0.65 g of 2-(n-dodecylamino)-1-(3-hydroxypropyl)-4-(3-hydroxypropylamino)-pyrimidinium bromide as an oil.

Employing the procedures, substantially as described in Examples 1 and 2, but substituting for the 2,4-dichloropyrimidine, n-dodecylamine, ethanolamine and methyl iodide used therein, comparable stoichiometric amounts respectively of the substituted pyrimidines, amines and alkyl halides described in Tables I and II there are produced 1-$R^1$-2-R-4-$R^4R^5$amino- 5(or 6)-$R^6$- pyrimidinium halides, also described in Tables I and II, in accordance with the following reaction scheme:

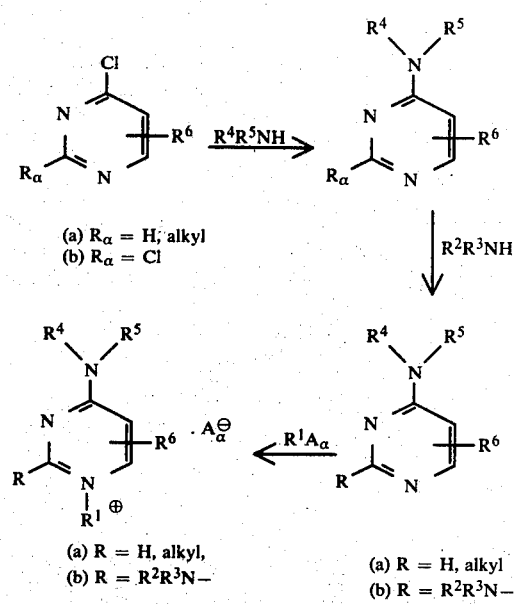

TABLE I

| R¹ | R² | R³ | R⁴ | R⁵ | R⁶ | A⊖ |
|---|---|---|---|---|---|---|
| —CH₂COOCH₃ | n-C₆H₁₃— | H | n-C₆H₁₃— | H | H | Br |
| n-C₁₂H₂₅— | HOC₂H₄— | H | (tetrahydrofuran-2-yl)CH₂— | H | H | Br |
| n-C₁₂H₂₅— | H | H | (tetrahydrofuran-2-yl)CH₂— | H | H | Br |
| n-C₁₂H₂₅— | HOC₂H₄— | H | CH₂=C(CH₃)—CH₂— | CH₂=C(CH₃)—CH₂— | H | Br |
| n-C₆H₁₃— | HOC₂H₄— | H | CH₂=C(CH₃)—CH₂— | CH₂=C(CH₃)—CH₂— | H | Br |
| n-C₆H₁₃— | (tetrahydrofuran-2-yl)CH₂— | H | (tetrahydrofuran-2-yl)CH₂— | H | H | Br |
| —CH₃ | HOC₂H₄— | H | n-C₄H₉CH(C₂H₅)CH₂— | n-C₄H₉CH(C₂H₅)CH₂— | H | I |
| n-C₆H₁₃— | HOC₂H₄— | H | (tetrahydrofuran-2-yl)CH₂— | H | H | Br |
| —CH₃ | HOC₂H₄— | H | n-C₆H₁₃— | n-C₆H₁₃— | 6-CH₃ | I |
| —CH₃ | HOC₂H₄— | H | n-C₈H₁₇— | n-C₈H₁₇— | H | I |
| —CH₃ | NH₂CH₂CHOHCH₂— | H | n-C₆H₁₃— | n-C₆H₁₃— | H | I |
| HOC₃H₆— | n-C₁₂H₂₅— | H | H | H | H | Br |
| n-C₁₂H₂₅— | HOC₂H₄— | H | HOC₂H₄— | H | H | Br |
| HOC₃H₆— | HOC₂H₄— | H | n-C₁₂H₂₅— | H | H | Br |
| cyclohexyl-CH₂CH₂— | HOC₂H₄— | H | cyclohexyl-CH₂— | H | H | Br |
| cyclohexyl-CH₂CH₂— | HOC₂H₄— | H | cyclohexyl-CH₂— | H | H | Br |
| n-C₁₂H₂₅— | HOC₂H₄— | H | C₆H₅-CH₂— | H | H | Br |
| CH₃— | HOC₂H₄— | H | H | H | H | Br |
| CH₂=C(CH₃)—CH₂— | HOC₂H₄— | H | n-C₁₈H₃₇— | H | H | Br |
| CH₂=C(CH₃)—CH₂— | HOC₂H₄— | H | n-C₁₂H₂₅— | H | H | I |
|  |  |  |  |  |  | Cl |
| HOC₃H₆— | n-C₆H₁₃— | H | n-C₆H₁₃— | H | H | Br |
| CH₃— | n-C₆H₁₃— | n-C₆H₁₃— | HOC₂H₄— | H | H | I |

TABLE I-continued

| $R^1$ | $R^2$ | $R^3$ | $R^4$ | $R^5$ | $R^6$ | $A_a^{\ominus}$ |
|---|---|---|---|---|---|---|
| $HOC_3H_6$— | $HOC_2H_4$— | H | $HOC_3H_6$— | H | H | Br |
| $CH_3$— | $n-C_{12}H_{25}$— | H | $n-C_{14}H_{29}$— | H | H | I |
| $CH_3$— | $HOC_2H_4$— | H | $HOC_3H_6$— | H | H | I |
| $CH_3$— | $HOC_3H_6$— | H | $n-C_{12}H_{25}$— | H | H | I |
| $HOC_3H_6$— | $HOC_3H_6$— | H | $n-C_{12}H_{25}$— | H | H | Br |
| $CH_3$— | $HOCH_2CHOHCH_2$— | H | $n-C_{12}H_{25}$— | H | H | I |
| $CH_3$— | $HOC_2H_4$— | H | $n-C_{12}H_{25}$— | H | 6-$CH_3$ | I |
| $CH_3$— | $HOC_2H_4$— | $n-C_6H_{13}$— | $HOC_2H_4$— | H | H | I |
| $n-C_{12}H_{25}$— | $CH_3$— | $CH_3$— | $HOC_2H_4$— | H | H | Cl |
| $CH_2=C-CH_2-$<br>$\quad\quad\vert$<br>$\quad\quad CH_3$ | $HOC_2H_4$— | H | $n-C_{12}H_{25}$— | H | H | Br |
| $n-C_{12}H_{25}$— | $HOC_2H_4$— | H | $HOC_2H_4$— | H | H | Cl |
| $n-C_{14}H_{29}$— | $CH_3OC_2H_4$— | H | $CH_3OC_2H_4$— | H | H | Br |
| $CH_3$— | $HOCH_2CH-CH_2-$<br>$\quad\quad\quad\vert$<br>$\quad\quad\quad OH$ | $CH_3$ | $n-C_6H_{13}$— | $n-C_6H_{13}$— | H | Br |
| (cyclohexyl)$CH_2$— | $C_2H_5OC_2H_4$— | H | $\begin{array}{c}C_2H_5\\\vert\\CH_3(CH_2)CHCH_2-\end{array}$ | $CH_3$— | H | Cl |
| $HOC_3H_6$— | $n-C_6H_{13}$— | H | $n-C_6H_{13}$— | H | H | Br |
| —$CH_2COOH$ | $CH_3OC_2H_4OC_2H_4$— | H | $n-C_4H_9$ | H | H | Br |
| $CH_3OC_2H_4$— | (benzyl $CH_2$—) | H | $n-C_8H_{17}$— | H | 6-$CH_3$ | Br |
| —$C_2H_4COOCH_3$ | (2-tetrahydrofuranyl-$CH_2$—) | H | $n-C_{12}H_{25}$— | H | 5-Cl | Br |
| $\begin{array}{c}O\\\Vert\\CH_3CCH_2-\end{array}$ | (p-$CH_3O$-benzyl) | $C_2H_5$ | $n-C_{10}H_{21}$— | $n-C_2H_5$ | H | Cl |
| $\begin{array}{c}C_2H_5O\\\quad\diagdown\\\quad\quad CH-\\\quad\diagup\\C_2H_5O\end{array}$ | $CH_3$— | $CH_3$ | $n-C_7H_{15}$— | $n-C_7H_{15}$— | 5-$CH_3$—$OC_2H_4$— | Br |
| $n-C_{12}H_{25}OC_2H_4$— | $HOC_2H_4$— | $i-C_3H_7$— | $n-C_{12}H_{25}$— | H | $\begin{array}{c}5\\6\end{array}\Big](CH_2)_3$ | I |
| $CH_3$— | —$CH_2COOH$ | —$CH_2COOH$ | $n-C_6H_{13}$— | $n-C_6H_{13}$— | 6-$CH_3$ | Br |
| $CH_3$— | $n-C_6H_{13}$— | $n-C_8H_{17}$— | $(HOCH_2)_3C$— | H | H | Cl |
| $t-C_4H_9$— | (p-benzyl-$CH_2$—) | $CH_3$ | $\begin{array}{c}C_2H_5\\\vert\\CH_3(CH_2)_3CH-CH_2-\end{array}$ | $HOC_2H_4$— | H | Br |

TABLE I-continued

| R¹ | R² | R³ | R⁴ | R⁵ | R⁶ | A⊖_a |
|---|---|---|---|---|---|---|
| HOCH₂CH(OH)CH₂— | n-C₄H₉— | n-C₄H₉— | n-C₁₂H₂₅— | H | H ⌐(CH₂)₄⌐ | Br |
| (tetrahydrofuran-2-yl)CH₂— | n-C₆H₁₃— | H | n-C₆H₁₃— | H | H | Br |
| n-C₁₂H₂₅— | (tetrahydrofuran-2-yl)CH₂— | H | (tetrahydrofuran-2-yl)CH₂— | HOC₃H₆— | H | Cl |
| (cyclopropyl)HOC₃H₆— | HOC₂H₄— | HOC₂H₄ | n-C₆H₁₃— | n-C₆H₁₃ | H | Br |
| HOC₃H₆— | cyclohexyl | H | cyclohexyl | n-C₁₀H₂₁ | H | Br |

TABLE II

| R¹ | R | R⁴ | R⁵ | R⁶ | A⊖ |
|---|---|---|---|---|---|
| CH₃— | CH₃— | n-C₁₂H₂₅— | H | 6-CH₂COOC₄H₉ | I |
| —CH₂CH₂COO⊖ | H | n-C₆H₁₃— | n-C₆H₁₃— | H | — |
| n-C₁₂H₂₅— | H | n-C₃H₇— | H | 5-CH₃SO— | Br |
| n-C₁₂H₂₅— | H | (tetrahydrofurfuryl)-CH₂— | H | 5-Cl | Br |
| n-C₁₂H₂₅— | H | (tetrahydrofurfuryl)-CH₂ | H | 6-CH₃ | Br |
| n-C₁₂H₂₅— | H | C₂H₅OC₂H₄— | C₂H₅OC₂H₄— | H | Br |
| n-C₁₂H₂₅— | H | (tetrahydrofurfuryl)-CH₂ | H | H | Br |
| n-C₁₂H₂₅— | H | (2-oxopyrrolidin-1-yl)—CH₂CH₂CH₂ | H | H | Br |
| CH₃— | H | HOC₂H₄— | n-C₁₄H₂₉— | H | I |
| CH₃— | CH₃— | n-C₁₃H₂₇CO— | H | 6-CH₃— | I |
| n-C₁₂H₂₅— | H | HOC₂H₄OC₂H₄— | H | H | Br |
| n-C₁₂H₂₅— | H | —CH₂—(uracil-5-yl) | H | H | Cl |
| HOC₃H₆— | H | n-C₄H₉CH(C₂H₅)CH₂— | H | H | Br |
| —CH₂CH(OC₂H₅)(OC₂H₅) | H | n-C₁₂H₂₅— | H | H | Br |
| —(CH₂)₆NHCOOCH₂—C₆H₅ | H | n-C₁₂H₂₅— | H | H | I |
| —CH₂CH=CHCOOC₂H₅ | H | n-C₁₂H₂₅— | H | H | Br |
| n-C₁₂H₂₅— | H | CH₃CHOHCH₂— | H | H | Br |
| CH₃COOCH₂CH₂— | H | n-C₁₂H₂₅— | H | H | Br |
| HOC₃H₆— | H | n-C₆H₁₃— | H | H | Br |
| HOC₃H₆— | H | n-C₆H₁₃— | n-C₆H₁₃— | H | Br |
| n-C₁₂H₂₅— | H | HOC₂H₄— | HOC₂H₄— | H | Br |
| CH₃OC₂H₄— | H | n-C₁₂H₂₅— | H | H | Br |
| HOC₃H₆— | H | n-C₁₂H₂₅— | H | H | Br |
| n-C₁₂H₂₅— | H | CH₃OC₂H₄— | H | H | Br |
| n-C₁₂H₂₅— | H | HOC₃H₆— | H | H | Br |
| HO(CH₂)₁₁— | CH₃— | H | H | 5-CH₃OCH₂— | Br |

EXAMPLE 3

1,6-Dimethyl-4-(n-dodecylamino)-2-(2-hydroxyethylamino)pyrimidinium acetate

To a solution of 1,6-dimethyl-4-(n-dodecylamino)-2-(2-hydroxyethylamino)pyrimidinium iodide (1.19 g, 0.0025 m) in a stirred mixture of water (10 ml) and 2-propanol (10 ml) at room temperature, is added silver acetate (0.44 g, 0.0026 m). An immediate yellow green precipitate forms. After allowing the stoppered mixture to stir overnight, the reaction mixture is filtered and the filtrate is concentrated under reduced pressure at room temperature to yield 1.0 g of 1,6-dimethyl-4-(n-dodecylamino)-2-(2-hydroxyethylamino)pyrimidinium acetate, m.p. 69°–74° C. with some softening at 58° C.

Employing the procedure substantially as described in Example 3, but substituting for the particular pyrimidinium halide silver acetate used therein, comparable respective stoichometric amounts of the pyrimidinium halides and silver salts described in Table III, there are produced the pyrimidinium salts also described in Table III in accordance with the following reaction scheme:

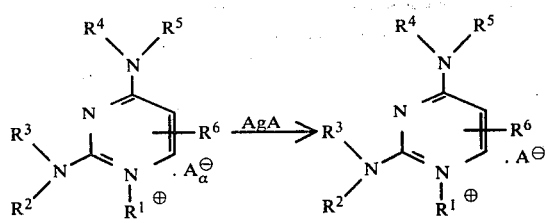

TABLE III

| $R^1$ | $R^2$ | $R^3$ | $R^4$ | $R^5$ | $R^6$ | $A_\alpha^-$ | $A^-$ |
|---|---|---|---|---|---|---|---|
| $CH_3-$ | $n\text{-}C_{12}H_{25}-$ | H | $HOC_3H_6-$ | H | H | Br | $CH_3COO$ |
| $CH_3OC_2H_4$ | $\langle\text{Ph}\rangle\text{-}C_2H_4$ | H | $n\text{-}C_8H_{17}-$ | H | $6\text{-}CH_3-$ | Br | $CH_3COO$ |
| $-C_2H_4-COOCH_3$ | tetrahydrofurfuryl-$CH_2-$ | H | $n\text{-}C_{12}H_{25}-$ | H | 5-Cl | Br | $NO_3$ |
| $CH_3-$ | $HOC_2H_4-$ | H | $n\text{-}C_{12}H_{25}-$ | H | $6\text{-}CH_3-$ | I | $CH_3COO$ |
| $CH_3-$ | $HOC_2H_4-$ | H | $n\text{-}C_{12}H_{25}-$ | H | H | I | $CH_3COO$ |

EXAMPLE 4

| Wettable Powder | lbs. |
|---|---|
| 4-n-Dodecylamino-2-(2-hydroxy-ethylamino)-1-(2-methyl-2-propenyl)-pyrimidinium chloride, powdered | 25 |
| Kaolin clay, finely powdered | 73 |
| Nonylphenoxypolyethoxyethanol | 2 |

The clay and pyrimidinium salt are intimately mixed as in a ribbon blender and the wetting agent introduced slowly ($\approx 15$ minutes) during the mixing operation. About 10 to 40 lbs. of the formulation can be suspended in 30 to 60 gallons of water and used to treat an acre of farm by spraying into furrows at planting time.

EXAMPLE 5

| Dispersible Paste | lbs. |
|---|---|
| 4-n-Dodecylamino-1-(2-methoxyethyl)-pyrimidinium bromide, powdered | 95 |
| Methycellulose | 2 |
| $C_{16}$–$C_{18}$ alkylbenzyldimethylammonium chloride | 3 |

The blending operation is performed similarly to preparing the wettable powder, with the surfactant added slowly to the powder mix. Sufficient water is added, from 25 to 50% by weight of the mixture, to provide a paste. Upon use about 5 lbs. of active ingredient containing paste is added to 50–60 gallons of water for soil application over an acre. When mixed to a depth of approximately three inches approximately 5 ppm of antimicrobial agent will be present.

| Emulsifiable Liquid | lbs. |
|---|---|
| 4-Di-n-hexylamino-2-(2-hydroxyethyl-amino)-1,6-dimethylpyrimidinium bromide, powdered | 5 |
| Dipropyleneglycolmonomethyl ether | 50 |
| Xylene, anhydrous | 40 |

| Emulsifiable Liquid -continued | lbs. |
|---|---|
| Alkylphenoxypolyethoxyethanol | 5 |

The wetting agent and one-half of each of the two solvents are added to a mixing tank fitted with a high speed disperser. The pyrimidinium bromide salt is added gradually with high speed agitation. After thorough dispersal the concentrate is let down into the remainder of the solvent mixture.

50–100 Lbs. of this preparation is made into an emulsion with 30 to 60 gallons of water and is sprayed on an acre of tomato or pepper to prevent attack and damage by bacterial leaf spot.

This formulation may also be used to control leaf spot of cabbage. About 150 gallons which contains 3 lbs. of the antimicrobial should be sprayed about 7–10 days after planting and should be re-applied weekly at the same rate as long as the disease is present. Early and late blight of celery is treated similarly.

EXAMPLE 6

| Dust | lbs. |
|---|---|
| 4-n-Dodecylamino-1-(3-hydroxy-propyl)pyrimidinium bromide, finely powdered | 75 |
| Vermiculite, finely powdered | 20 |
| Polyethyleneglycol #5000: Ethyleneglycol (1:1) | 5 |

The first two components are thoroughly dry blended and the last mixture gradually added during mixing.

The dust is simply mixed with seed in a closed tumbling device commonly employed on small farms. The rate is from about 2 oz. dust per 100 lbs. bean seed to prevent seed decay and damping-off, or about 6 ozs./100 lbs. for beet seed.

What is claimed is:

1. A compound of structural formula:

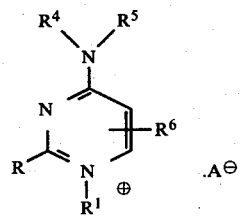

wherein
R is hydrogen, $C_{1-5}$ alkyl or $R^2R^3N-$;
$R^1$ is
  (1) $C_{2-5}$ alkenyl
  (2) $C_{1-3}$ alkoxycarbonyl-$C_{2-5}$ alkenyl,
  (3) $C_{1-18}$ alkyl, or
  (4) $C_{1-18}$ alkyl mono-substituted with
    (a) hydroxy
    (b) $C_{1-3}$ alkoxy
    (c) carboxy,
    (d) $C_{1-3}$ alkoxycarbonyl,
    (e) $C_{2-5}$ alkanoyloxy,
    (f) $C_{3-6}$ cycloalkyl,
    (g) gem-di ($C_{1-3}$ alkoxy),
    (h) tetrahydrofuranyl,
    (i) hydroxy-$C_{1-3}$ alkoxy, or
    (j) $C_{2-3}$ alkanoyl,
$R^2$, $R^3$, $R^4$ and $R^5$ are independently
  (1) hydrogen, or
  (2) $R^1$;
$R^6$ is
  (1) hydrogen,
  (2) $C_{1-11}$ alkyl,
  (3) $C_{1-5}$ alkoxy-$C_{1-11}$ alkyl,
  (4) $C_{1-5}$ alkoxycarbonyl-$C_{1-11}$ alkyl,
  (5) $C_{1-3}$ alkylsulfinyl, or
  (6) $-(CH_2)_n-$ wherein n is 3 or 4 and the group $-(CH_2)_n-$ is joined to the 5 and 6 carbons of the pyrimidine ring; and
$A^\ominus$ is a non-toxic anion derived from an organic or inorganic acid; with the proviso that;
  (1) at least one of $R^{1-5}$ is $C_{6-18}$ alkyl,
  (2) at least one of $R^{1-5}$ is oxygen bearing, and
  (3) at least one exocyclic nitrogen is a secondary or tertiary amine.

2. The compound of claim 1, wherein R is $R^2R^3N-$.

3. The compound of claim 2, wherein $R^1$ is $C_{1-5}$ alkyl, hydroxy-$C_{1-5}$ alkyl, or $C_{3-5}$ alkenyl; one of $R^2R^3N-$ and $R^4R^5N-$ is hydroxy-$C_{1-5}$ alkyl-NH— and the other is $C_{12}$ alkyl-NH- or di($C_6$ alkyl)N—; $R^6$ is hydrogen or $C_{1-3}$ alkyl; and $A^-$ is halide, or acetate.

4. The compound of claim 3 which is 4-(n-dodecylamino)-2-(2-hydroxyethylamino)-1-methyl-pyrimidinium chloride, bromide, iodide, or acetate.

5. The compound of claim 3 which is 4-(n-dodecylamino)-2-(2-hydroxyethylamino)-1-(2-methyl-2-propenyl)pyrimidinium chloride or bromide.

6. The compound of claim 3 which is 2-(n-dodecylamino)-1-(3-hydroxypropyl)-4-(3-hydroxypropylamino)pyrimidinium chloride, bromide or iodide.

7. The compound of claim 3 which is 4-(di-n-hexylamino)-2-(2-hydroxyethylamino)-1-methyl-pyrimidinium bromide.

8. The compound of claim 3 which is 1,6-dimethyl-4-(n-dodecylamino)-2-(2-hydroxyethylamino)-pyrimidinium acetate.

9. 2,4-Bis-(n-hexylamino)-1-(3-hydroxypropyl)-pyrimidinium bromide.

10. 4-n-Dodecylamino-1-(3-hydroxypropyl)-pyrimidinium bromide.

11. 1-n-Dodecyl-4-[(2-methoxyethyl)amino]-pyrimidinium bromide.

12. An antimicrobial composition comprising a carrier and an effective antimicrobial amount of a compound of structural formula:

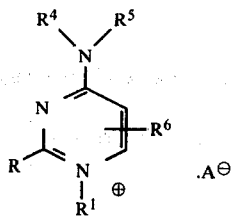

wherein
R is hydrogen, $C_{1-5}$ alkyl or $R^2R^3N$-;
$R^1$ is
  (1) $C_{2-5}$ alkenyl,
  (2) $C_{1-3}$ alkoxycarbonyl-$C_{2-5}$ alkenyl,
  (3) $C_{1-18}$ alkyl, or
  (4) $C_{1-18}$ alkyl mono-substituted with
    (a) hydroxy
    (b) $C_{1-3}$ alkoxy
    (c) carboxy
    (d) $C_{1-3}$ alkoxycarbonyl,
    (e) $C_{2-5}$ alkanoyloxy,
    (f) $C_{3-6}$ cycloalkyl,
    (g) gem-di ($C_{1-3}$ alkoxy),
    (h) tetrahydrofuranyl,
    (i) hydroxy-$C_{1-3}$ alkoxy, or
    (j) $C_{2-3}$ alkanoyl,
$R^2$, $R^3$, $R^4$ and $R^5$ are independently
  (1) hydrogen, or
  (2) $R^1$;
$R^6$ is
  (1) hydrogen,
  (2) $C_{1-11}$ alkyl,
  (3) $C_{1-5}$ alkoxy-$C_{1-11}$ alkyl,
  (4) $C_{1-5}$ alkoxycarbonyl-$C_{1-11}$ alkyl.
  (5) $C_{1-3}$ alkylsulfinyl, or
  (6) $-(CH_2)_n-$ wherein n is 3 or 4 and the group $-(CH_2)_n-$ is joined to the 5 and 6 carbons of the pyrimidine ring; and
$A^\ominus$ is a non-toxic anion derived from an organic or inorganic acid; with the proviso that;
  (1) at least one of $R^{1-5}$ is $C_{6-18}$ alkyl,
  (2) at least one of $R^{1-5}$ is oxygen bearing, and
  (3) at least one exocyclic nitrogen is a secondary or tertiary amine.

13. The composition of claim 12 wherein R is $R^2R^3N-$.

14. The composition of claim 13, wherein $R^1$ is $C_{1-5}$ alkyl, hydroxy-$C_{1-5}$ alkyl, or $C_{3-5}$ alkenyl; one of $R^2R^3N$- and $R^4R^5N$- is hydroxy-$C_{1-5}$ alkyl-NH— and the other is $C_{12}$-alkyl-NH— or di($C_6$ alkyl)N—; $R^6$ is hydrogen or $C_{1-5}$ alkyl; and $A^\ominus$ is halide, or acetate.

15. A method of inhibiting microbial growth which comprises the application of an effective antimicrobial amount of a compound of structural formula:

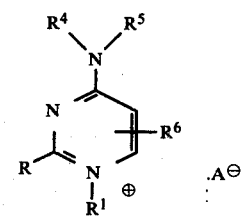

wherein

R is hydrogen, $C_{1-5}$ alkyl or $R^2R^3N-$;
$R^1$ is
  (1) $C_{2-5}$ alkenyl,
  (2) $C_{1-3}$ alkoxycarbonyl-$C_{2-5}$ alkenyl,
  (3) $C_{1-18}$ alkyl, or
  (4) $C_{1-18}$ alkyl mono-substituted with
    (a) hydroxy
    (b) $C_{1-3}$ alkoxy
    (c) carboxy,
    (d) $C_{1-3}$ alkoxycarbonyl,
    (e) $C_{2-5}$ alkanoyloxy,
    (f) $C_{3-6}$ cycloalkyl,
    (g) gemi-di ($C_{1-3}$ alkoxy),
    (h) tetrahydrofuranyl,
    (i) hydroxy-$C_{1-3}$ alkoxy, or
    (j) $C_{2-3}$ alkanoyl,
$R^2$, $R^3$, $R^4$ and $R^5$ are independently
  (1) hydrogen, or
  (2) $R^1$;
$R^6$ is
  (1) hydrogen,
  (2) $C_{1-11}$ alkyl,
  (3) $C_{1-5}$ alkoxy-$C_{1-11}$ alkyl,
  (4) $C_{1-5}$ alkoxycarbonyl-$C_{1-11}$ alkyl,
  (5) $C_{1-3}$ alkylsulfinyl, or
  (6) $-(CH_2)_n-$ wherein n is 3 or 4 and the group $-(CH_2)_n-$ is joined to the 5 and 6 carbons of the pyrimidine ring; and
$A^{\ominus}$ is a non-toxic anion derived from an organic or inorganic acid; with the proviso that;
  (1) at least one of $R^{1-5}$ is $C_{6-18}$ alkyl,
  (2) at least one of $R^{1-5}$ is oxygen bearing, and
  (3) at least one exocyclic nitrogen is a secondary or tertiary amine.

16. The method of claim 15, wherein R is $R^2R^3N-$.

17. The method of claim 16, wherein $R^1$ is $C_{1-5}$ alkyl, hydroxy-$C_{1-5}$ alkyl, or $C_{3-5}$ alkenyl; one of $R^2R^3N-$ and $R^4R^5N-$ is hydroxy-$C_{1-5}$ alkyl-NH— and the other is $C_{12}$-alkyl-NH— or di($C_6$ alkyl)N—; $R^6$ is hydrogen or $C_{1-3}$ alkyl; and $A^{\ominus}$ is halide, or acetate.

18. The method of protecting seeds and plants against fungal and bacterial attack which comprises applying to the soil, seed or plant an antifungal and antibacterial amount of a composition the active ingredient of which is a compound of structural formula:

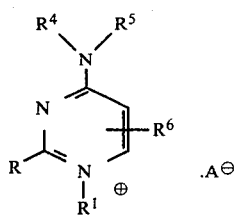

wherein
R is hydrogen, $C_{1-5}$ alkyl or $R^2R^3N-$;
$R^1$ is
  (1) $C_{2-5}$ alkenyl,
  (2) $C_{1-3}$ alkoxycarbonyl-$C_{2-5}$ alkenyl,
  (3) $C_{1-18}$ alkyl, or
  (4) $C_{1-18}$ alkyl mono-substituted with
    (a) hydroxy
    (b) $C_{1-3}$ alkoxy
    (c) carboxy,
    (d) $C_{1-3}$ alkoxycarbonyl,
    (e) $C_{2-5}$ alkanoyloxy,
    (f) $C_{3-6}$ cycloalkyl,
    (g) gem-di ($C_{1-3}$ alkoxy),
    (h) tetrahydrofuranyl,
    (i) hydroxy-$C_{1-3}$ alkoxy, or
    (j) $C_{2-3}$ alkanoyl,
$R^2$, $R^3$, $R^4$ and $R^5$ are independently
  (1) hydrogen, or
  (2) $R^1$;
$R^6$ is
  (1) hydrogen,
  (2) $C_{1-11}$ alkyl,
  (3) $C_{1-5}$ alkoxy-$C_{1-11}$ alkyl,
  (4) $C_{1-5}$ alkoxycarbonyl-$C_{1-11}$ alkyl,
  (5) $C_{1-3}$ alkylsulfinyl, or
  (6) $-(CH_2)_n-$ wherein n is 3 or 4 and the group $-(CH_2)_n-$ is joined to the 5 and 6 carbons of the pyrimidine ring; and
$A^{\ominus}$ is a non-toxic anion derived from an organic or inorganic acid; with the proviso that;
  (1) at least one of $R^{1-5}$ is $C_{6-18}$ alkyl,
  (2) at least one of $R^{1-5}$ is oxygen bearing, and
  (3) at least one exocyclic nitrogen is a secondary or tertiary amine.

19. The method of claim 18, wherein R is $R^2R^3N-$.

20. The method of claim 19, wherein $R^1$ is $C_{1-5}$ alkyl, hydroxy-$C_{1-5}$ alkyl, or $C_{3-5}$ alkenyl; one of $R^2R^3N-$ and $R^4R^5N-$ is hydroxy-$C_{1-5}$ alkyl-NH— and the other is $C_{12}$ alkyl-NH— or di($C_6$ alkyl)N—; $R^6$ is hydrogen or $C_{1-3}$ alkyl; and $A^{\ominus}$ is halide, or acetate.

* * * * *